(12) United States Patent (10) Patent No.: US 8,571,277 B2
Suri et al. (45) Date of Patent: Oct. 29, 2013

(54) IMAGE INTERPOLATION FOR MEDICAL IMAGING

(75) Inventors: Jasjit S. Suri, Roseville, CA (US); Dinesh Kumar, Grass Valley, CA (US)

(73) Assignee: Eigen, LLC, Grass Valley, CA (US)

( * ) Notice: Subject to any disclaimer, the term of this patent is extended or adjusted under 35 U.S.C. 154(b) by 1351 days.

(21) Appl. No.: 11/874,778

(22) Filed: Oct. 18, 2007

(65) Prior Publication Data

US 2009/0103791 A1 Apr. 23, 2009

(51) Int. Cl.
*G06K 9/00* (2006.01)
(52) U.S. Cl.
USPC .......................................... 382/128; 382/154
(58) Field of Classification Search
USPC .................................................. 382/128, 154
See application file for complete search history.

(56) References Cited

U.S. PATENT DOCUMENTS

| | | | |
|---|---|---|---|
| 5,282,472 A | 2/1994 | Companion et al. | |
| 5,320,101 A | 6/1994 | Faupel et al. | |
| 5,383,454 A | 1/1995 | Bucholz | |
| 5,398,690 A | 3/1995 | Batten et al. | |
| 5,454,371 A | 10/1995 | Fenster et al. | |
| 5,531,520 A * | 7/1996 | Grimson et al. | 382/131 |
| 5,562,095 A | 10/1996 | Downey et al. | |
| 5,611,000 A | 3/1997 | Szeliski et al. | |
| 5,810,007 A | 9/1998 | Holupka et al. | |
| 5,842,473 A | 12/1998 | Fenster et al. | |
| 6,047,080 A * | 4/2000 | Chen et al. | 382/128 |
| 6,092,059 A | 7/2000 | Straforini et al. | |
| 6,171,249 B1 | 1/2001 | Chin et al. | |
| 6,238,342 B1 | 5/2001 | Feleppa et al. | |
| 6,251,072 B1 | 6/2001 | Ladak et al. | |
| 6,261,234 B1 | 7/2001 | Lin | |
| 6,298,148 B1 | 10/2001 | Cline et al. | |
| 6,334,847 B1 | 1/2002 | Fenster et al. | |
| 6,342,891 B1 | 1/2002 | Fenster et al. | |
| 6,351,547 B1 * | 2/2002 | Johnson et al. | 382/128 |
| 6,351,660 B1 | 2/2002 | Burke et al. | |
| 6,360,027 B1 | 3/2002 | Hossack et al. | |
| 6,385,332 B1 | 5/2002 | Zahalka et al. | |
| 6,423,009 B1 | 7/2002 | Downey et al. | |
| 6,447,477 B2 | 9/2002 | Burney et al. | |
| 6,461,298 B1 * | 10/2002 | Fenster et al. | 600/437 |
| 6,500,123 B1 | 12/2002 | Holloway et al. | |
| 6,561,980 B1 | 5/2003 | Gheng et al. | |
| 6,567,687 B2 | 5/2003 | Front et al. | |
| 6,610,013 B1 | 8/2003 | Fenster et al. | |
| 6,611,615 B1 | 8/2003 | Christensen | |

(Continued)

FOREIGN PATENT DOCUMENTS

| | | |
|---|---|---|
| WO | 0014668 | 3/2000 |
| WO | 2006089426 A1 | 8/2006 |
| WO | 2008062346 A1 | 5/2008 |
| WO | 2008124138 A1 | 10/2008 |

*Primary Examiner* — Hadi Akhavannik
(74) *Attorney, Agent, or Firm* — Russell T. Manning; Marsh Fischmann & Breyfogle LLP

(57) ABSTRACT

Presented are systems and methods that allow for interpolation of a 3-D volume from arbitrarily oriented 2-D medical images. The interpolation of 3-D volume from arbitrarily oriented 2-D images reduces or eliminates most constraints on image acquisition thereby allowing for, inter alia, freehand manipulation of an image acquisition device (e.g. an ultrasound transducer). Related utilities involve the use of prior information about a specific object of interest to interpolate a surface (e.g., 3-D surface) of the object from limited information obtained from very few 2-D images.

13 Claims, 7 Drawing Sheets

(56) References Cited

U.S. PATENT DOCUMENTS

| | | |
|---|---|---|
| 6,674,916 B1 | 1/2004 | Deman et al. |
| 6,675,032 B2 | 1/2004 | Chen et al. |
| 6,675,211 B1 | 1/2004 | Mamaghani et al. |
| 6,689,065 B2 | 2/2004 | Aksnes et al. |
| 6,778,690 B1 | 8/2004 | Ladak et al. |
| 6,824,516 B2 | 11/2004 | Batten et al. |
| 6,842,638 B1 | 1/2005 | Suri et al. |
| 6,852,081 B2 | 2/2005 | Sumanaweera et al. |
| 6,909,792 B1 | 6/2005 | Carrott et al. |
| 6,952,211 B1 | 10/2005 | Cote et al. |
| 6,985,612 B2 | 1/2006 | Hahn |
| 7,004,904 B2 | 2/2006 | Chalana et al. |
| 7,008,373 B2 | 3/2006 | Stoianovici et al. |
| 7,039,216 B2 | 5/2006 | Shum et al. |
| 7,039,239 B2 | 5/2006 | Loui et al. |
| 7,043,063 B1 | 5/2006 | Noble et al. |
| 7,095,890 B2 | 8/2006 | Paragois et al. |
| 7,119,810 B2 | 10/2006 | Sumanaweera et al. |
| 7,139,601 B2 | 11/2006 | Bucholz et al. |
| 7,148,895 B2 | 12/2006 | Konishi et al. |
| 7,155,316 B2 | 12/2006 | Sutherland et al. |
| 7,162,065 B2 | 1/2007 | Ladak et al. |
| 7,167,760 B2 | 1/2007 | Dawant et al. |
| 7,225,012 B1 | 5/2007 | Susil et al. |
| 7,274,811 B2 | 9/2007 | Sirohey et al. |
| 7,298,881 B2 * | 11/2007 | Giger et al. .................. 382/128 |
| 7,302,092 B1 | 11/2007 | Fenster et al. |
| 7,403,646 B2 | 7/2008 | Sato |
| 7,519,206 B2 * | 4/2009 | Mulet-Parada et al. ....... 382/128 |
| 2003/0000535 A1 | 1/2003 | Galloway, Jr. et al. |
| 2003/0135115 A1 | 7/2003 | Burdette et al. |
| 2004/0081340 A1 * | 4/2004 | Hashimoto .................. 382/128 |
| 2004/0210133 A1 | 10/2004 | Nir |
| 2005/0027188 A1 * | 2/2005 | Metaxas et al. ............... 600/410 |
| 2005/0159676 A1 | 7/2005 | Taylor et al. |
| 2005/0190189 A1 | 9/2005 | Chefd'hotel et al. |
| 2005/0197977 A1 | 9/2005 | Buck et al. |
| 2005/0243087 A1 | 11/2005 | Aharon |
| 2005/0249398 A1 | 11/2005 | Khamene et al. |
| 2006/0002601 A1 | 1/2006 | Fu et al. |
| 2006/0002630 A1 | 1/2006 | Fu et al. |
| 2006/0013482 A1 | 1/2006 | Dawant et al. |
| 2006/0036162 A1 | 2/2006 | Shahidi et al. |
| 2006/0074297 A1 * | 4/2006 | Viswanathan ................ 600/424 |
| 2006/0079771 A1 | 4/2006 | Nir |
| 2006/0197837 A1 | 9/2006 | Flath et al. |
| 2006/0227131 A1 | 10/2006 | Schiwietz et al. |
| 2006/0258933 A1 | 11/2006 | Ellis et al. |
| 2006/0285755 A1 * | 12/2006 | Hager et al. .................. 382/224 |
| 2007/0014446 A1 | 1/2007 | Sumanaweera et al. |
| 2007/0040830 A1 | 2/2007 | Papageorgiou |
| 2007/0081703 A1 * | 4/2007 | Johnson ....................... 382/128 |
| 2007/0116339 A1 | 5/2007 | Shen |
| 2007/0116381 A1 | 5/2007 | Khamene |
| 2007/0189603 A1 | 8/2007 | Kasperkiewicz et al. |
| 2007/0201611 A1 | 8/2007 | Pratx et al. |
| 2007/0219448 A1 * | 9/2007 | Seip et al. ..................... 600/454 |
| 2007/0270687 A1 | 11/2007 | Gardi et al. |
| 2008/0002870 A1 | 1/2008 | Farag et al. |
| 2008/0123910 A1 | 5/2008 | Zhu |
| 2008/0123927 A1 | 5/2008 | Miga et al. |
| 2008/0170770 A1 | 7/2008 | Suri et al. |
| 2008/0247616 A1 | 10/2008 | Pescatore et al. |
| 2008/0247622 A1 * | 10/2008 | Aylward et al. ............... 382/131 |
| 2009/0093715 A1 | 4/2009 | Downey et al. |

* cited by examiner

IMAGE INTERPOLATION FOR MEDICAL IMAGING

FIELD

The present disclosure pertains to the field of medical imaging, and more particular to the registration of arbitrarily aligned 2-D images to allow for the generation/reconstruction of a 3-D image/volume.

BACKGROUND

Medical imaging, including X-ray, magnetic resonance (MR), computed tomography (CT), ultrasound, and various combinations of these and other image acquisition modalities are utilized to provide images of internal patient structure for diagnostic purposes as well as for interventional procedures. Often, it is desirable to utilize multiple two-dimensional (i.e. 2-D) images to generate (e.g., reconstruct) a three-dimensional (i.e., 3-D) image of an internal structure of interest.

2-D image to 3-D image reconstruction has been used for a number of image acquisition modalities (such as MRI, CT, Ultrasound) and image based/guided procedures. These images may be acquired as a number of parallel 2-D image slices/planes or rotational slices/planes, which are then combined together to reconstruct a 3-D image volume. Generally, the movement of the imaging device has to be constrained such that only a single degree of freedom is allowed (e.g., rotation). This single degree of freedom may be rotation of the equipment or a linear motion. During such a procedure, the presence any other type of movement will typically cause the registration of 2-D images in 3-D space to be inaccurate. This presents some difficulties in handheld image acquisition where rigidly constraining movement of an imaging device to a single degree of freedom is difficult if not impossible. Further constraining an imaging device to a single degree of freedom may also limit the image information that may be acquired. This is true for handheld, automated and semi-automated image acquisition. Depending upon the constraints of the image acquisition methods, this may limit use or functionality the acquisition system for 3-D image generation.

Many 3-D reconstruction techniques currently require a significant number of 2-D images in order to achieve a reasonably good resolution. This typically results in a slow scan process and/or slow 3-D image reconstruction. The requirement of a large number of 2-D images may also lead to unnecessary workflow issues, causing hindrance to workflow and/or patient discomfort. Further, in many imaging situations, the actual region of interest is generally much smaller than the actual image acquired, resulting in unnecessary computational overheads for interpolation at regions outside the object of interest. During a medical procedure such as image based biopsy or therapy, a user is generally interested in only one organ and not in the background information. Further, in operating room environments time allocated for imaging procedures and/or image guide procedures is minimal due to time pressures on surgeons to undergo more procedures in allocated time. Accordingly, it is desirable to perform 3-D image generation in a manner that reduces the constraints on image acquisition and allows for quickly generating a 3-D image, while also providing sufficient resolution to perform a desired procedure.

SUMMARY

The invention presented herein solves a number of problems using novel systems and methods (i.e., utilities). These utilities allow for interpolation of a 3-D volume from arbitrarily oriented 2-D images. The interpolation of 3-D volume from arbitrarily oriented 2-D images reduces or eliminates most constraints on image acquisition thereby allowing for, inter alia, freehand manipulation of an image acquisition device (e.g. an ultrasound transducer). In one arrangement, the utilities maintain the relationship between acquired 2-D images and a prospective 3-D image volume via a tracker that tracks the coordinates and orientation of the imaging plane of each 2-D image. This can be done using any type of tracker including but not limited to optical, magnetic and/or mechanical trackers. It will be appreciated the interpolation methods are not limited by the method of tracking, imaging modality or type of procedure. The interpolation method is not limited to ultrasound but applicable to other modalities such as MRI, CT, PET, SPECT and its fusion.

A related utility involves the use of prior information about a specific object of interest to interpolate a surface (e.g., 3-D surface) of the object from limited information obtained from very few 2-D images. In this utility, shape statistics of a structure/object of interest are computed beforehand and stored in a computer. The prior shape statistics may include a mean shape of the object and/or the statistics over a large number of samples of the object of interest. This allows for generation of a shape based deformation model. Deformation of the shape based model may be guided (in real time) and constrained by the actual deformation statistics from the shape priors. The shape model is used to deform the mean shape of the object to the available 2-D images/planes through, for example, hierarchical optimization over the modes of variation of the object. The deformation may be guided by intensity gradients over the available 2-D images of arbitrary orientation. The inventive aspects may be implemented in processing systems that are integrated into medical imaging devices/systems and/or be implemented into stand-alone processing systems that interface with medical imaging devices/systems.

In one aspect, the utility is provided for allowing interpolation and/or reconstruction of a 3-D image based on arbitrarily oriented 2-D image planes obtained from a 2-D imaging device. The method includes obtaining at least first and second 2-D images of an internal object of interest. Each 2-D image includes an image plane and a first 3-D point of reference. Typically, the image planes and 3-D points of reference are different for each image. Pixel information (e.g., intensity information) for each of the 2-D images is translated into a common 3-D volume. Based on the pixel information disposed within a common 3-D volume, a 3-D image of the object of interest is generated.

Translating the pixel information of the 2-D images into a common 3-D volume may include applying a coordinate transform to the 2-D images. As may be appreciated, this may require obtaining or otherwise determining vector information for use with the images. Typically, the 3-D point of reference may be provided by a tracker assembly that provides location information for a medical imaging device that generates the 2-D image. Furthermore, information regarding the depth and orientation of the image in relation to the reference point may also be obtained. Accordingly, a normal may be determined for the plane of the 2-D image. Utilizing this information, a transformation matrix may be applied to the vector information associated with the 2-D images. Accordingly, such transformation may allow for translating pixels within the 2-D images into the common 3-D volume. The method may further include interpolating pixel intensities from the 2-D images to discrete locations within the 3-D volume.

It will be appreciated that the ability to translate arbitrary 2-D images into a common 3-D volume avoids the need for a constrained image acquisition procedure. That is, no mechanical assembly is required for obtaining 2-D images. As a result, an imaging device may be freely maneuvered (e.g., freehand), which may result in better workflow.

Once a 3-D image is generated from the pixel information of the 3-D volume, the user may selectively obtain additional 2-D images. This information may be incorporated into the 3-D image. This may allow a user to focus on specific parts of anatomy by acquiring samples non-uniformly. This provides the user with flexibility to acquire images in better resolutions at some regions while acquiring imaging at lower resolution at others. This not only enhances the resolution at desired locations but also reduces the unnecessary computational overhead of acquiring samples from locations where lower resolution may be adequate. Likewise, this may reduce the time required to adequately scan an object of interest.

In a further aspect, a shape model may be fit to pixel information in a common 3-D volume in order to define a 3-D surface of an internal object of interest. Accordingly, a plurality of arbitrarily aligned 2-D medical images may be obtained for an internal object of interest. Pixel intensity information from each of the 2-D images may be translated into a 3-D volume. Accordingly, a predefined shape model may be fit to the pixel intensity information such that the shape model defines a 3-D surface for the object of interest.

In one arrangement, the predefined shape model may be generated based on an average of a population of a corresponding object. For instance, for prostate imaging, such a shape model may be generated from a training set of prostate images. Likewise, shape statistics for the training set population may be utilized in order to fit the predefined shape model to the pixel intensity information. In a further arrangement, the shape model may be constrained by boundaries identified within the 2-D images. In this regard, segmentation may be performed on the 2-D images in order to identify one or more boundaries therein. These boundaries may then be utilized as constraints for the shape model.

In one arrangement, a principle component analysis is utilized to identify the largest modes of variation for the shape model. Accordingly, by identifying the largest modes of variation the shape model may be fit to the pixel intensities utilizing fewer variables.

In another aspect, the utility is provided for registering current two-dimensional images with previously stored three-dimensional images. In this regard, during an imaging procedure as a user manipulates an imaging instrument (e.g., freehand) previous few image frames may be kept in memory. These frames may then be used for motion correction of the current imaging device location relative to a previously acquired/stored three-dimensional image. Such motion correction may be necessitated due to patient movement, motion of anatomical structures to the procedure and/or to device movement or miscalibration. Initially, a series of two-dimensional images are obtained. The series of two-dimensional images may be obtained in real-time such that the last image is the most current image. Pixel information from each of the two-dimensional images may be translated into common three-dimensional volume in order to generate a current three-dimensional image using the series of two-dimensional images. This current three-dimensional image of the object of interest may be utilized to align the most current two-dimensional with the previously stored three-dimensional image.

In one arrangement, use of the current three-dimensional image may include registering the current three-dimensional image with the previous three-dimensional image in order to identify orientation correspondence therebetween. Accordingly, the most current two-dimensional image may be aligned based on this information.

In one arrangement, the two-dimensional images are maintained and buffer in the computerized imaging device. Such images may be maintained on a first and first-out basis. For instance, the buffer may maintain the previous five to 10 images wherein the oldest image is continuously replaced by the most current image.

Generally, all the utilities also allow for using more information during navigation. That is, the presented utilities use more information than most conventional 2-D ultrasound based navigation systems. This is done by keeping some of the previous image frames in a buffer. The previous frames together with the current frame provide at least partially 3-D information and thus provide a better and more robust solution when correlating the current 2-D image with an earlier acquired 3-D.

The utilities also allow for non-rigid motion correction. That is, in addition to correlating a current 2-D image with 3-D scan, the additional information can also be used to perform non-rigid registration. Since more frames are used, more deformation can be captured by the deformation model.

The utilities also permit shape based boundary interpolation. In this regard a mean shape model may be fit to the boundaries of an object based on much less information compared to an explicit segmentation method. The mean shape is used as the template for fitting onto the surface. By definition, mean shape is more similar to the population and thus, is ideal as the deformation template. Further usage of actual deformation statistics from the training samples (i.e., used to form the shape model) corresponding to the anatomy of the object in consideration represent actual deformation modes of the objects in the population and thus, the results are representative of the population.

Further, the use of reduced dimensionality of the shape model may allow for faster image generation speeds. In one arrangement, the presented utilities use a principal component analysis (PCA), which identifies and optimizes over a smaller number of parameters while capturing population statistics well. Further hierarchical optimization over modes of variations ensures that coefficients for larger modes get optimized first and then smaller modes of variations follow. This adds to robustness and stability of utilities and also avoids small local minima.

The utilities are also adaptable to image fusion with other imaging modalities. That is, the utilities are easily extensible to include image fusion (e.g., ultrasound images) with other modalities such as Elastography, MR spectroscopy, MRI, etc. The interpolated frames in the 3-D space can be correlated with the images from other modality and the correspondence computed between them.

The utilities also provide more information for tracking in 3-D. Due to dynamic nature of the placement of 2-D data in 3-D and arbitrariness of the orientation, the 2-D frames can be kept in memory buffer of the computer and called upon to correct for motion compensation in 3-D. Most current techniques only use the live 2-D image to correlate the current field of view, which is an ill-conditioned problem. Extra information present in form of previous frames makes it better conditioned.

The utilities can be used to compute local deformation at every place inside the object of interest, which can be used for clinical interpretation about the nature and progression of a disease. Many diseases including cancer manifest themselves into change in tissue deformation characteristics or change in tissue volume over time, which can be easily captured through computation of local deformation.

DETAILED DESCRIPTION

Reference will now be made to the accompanying drawings, which assist in illustrating the various pertinent features of the present disclosure. Although the present disclosure is described primarily in conjunction with transrectal ultrasound imaging for prostate imaging, it should be expressly understood that aspects of the present invention may be applicable to other medical imaging applications. In this regard, the following description is presented for purposes of illustration and description.

As presented, the invention is directed towards systems and methods for interpolation and reconstruction of a 3-D image from 2-D image planes/frames/slices obtained in arbitrary orientation during, for example, an unconstrained scan procedure. Also included is a method for adaptively improving interpolation based on dynamic addition of more 2-D frames to an imaging buffer. Systems and methods are also provided for using shape priors to interpolate the surface of an internal object of interest using intensity information of a limited number of 2-D image planes that have the object of interest in their field of view. Further, a combination of the above systems and methods allow arbitrary (e.g., freehand) scanning of a few 2-D images and then fitting a surface for the object of interest using intensity information from the scanned images.

The reconstruction method pertains to all types of 2-D image acquisition methods under various modalities and specifically for 2-D image acquisition methods used while performing an image-guided diagnostic or surgical procedure. It will be appreciated that such procedures include, but are not limited to ultrasound guided biopsy of various organs, such as prostate (trans-rectal and trans-perineal), liver, kidney, breast, etc., brachytherapy, ultrasound guided laparoscopy, ultrasound guided surgery or an image-guided drug delivery procedures.

As noted above, most current methods for reconstructing a 3-D image from 2-D image planes assume some type of uniformity (e.g., constraint) in image acquisition. For example, most previous methods assume (or require) that the 2-D images be obtained as parallel slices or are displaced from each other through an angle while meeting at one fixed axis.

Figure 1:
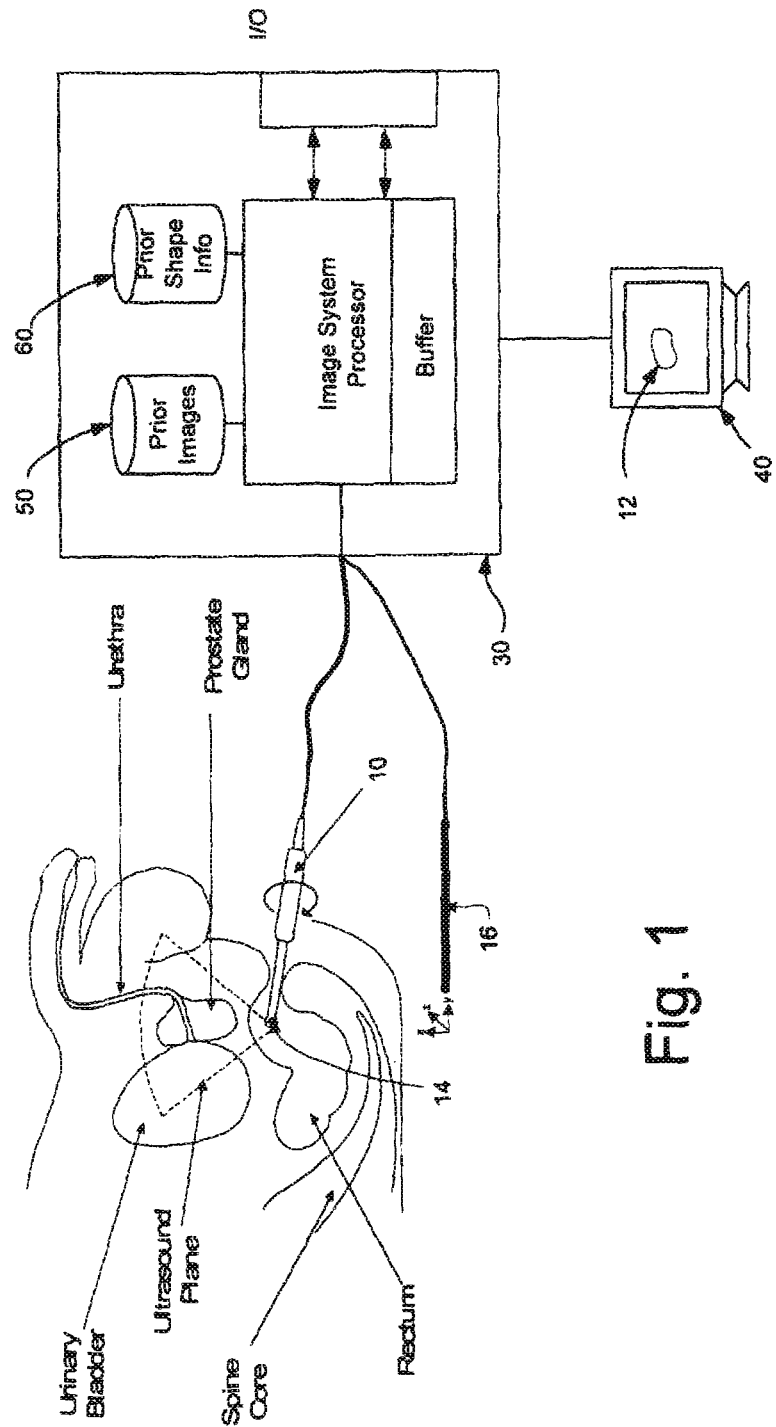
FIG. 1 illustrates a medical imaging system utilized for ultrasound imaging.

FIG. 1 illustrates a transrectal ultrasound probe 10 that may be utilized to obtain a plurality of two-dimensional ultrasound images of the prostate 12. As shown, the probe 10 may be operative to scan an area of interest. The probe 10 may also include a biopsy gun that may be attached to the probe. Such a biopsy gun may include a spring driven needle that is operative to obtain a core from desired area within the prostate and/or deliver medicine (e.g., a brachytherapy seed) to a location within the prostate.

Figure 2A:
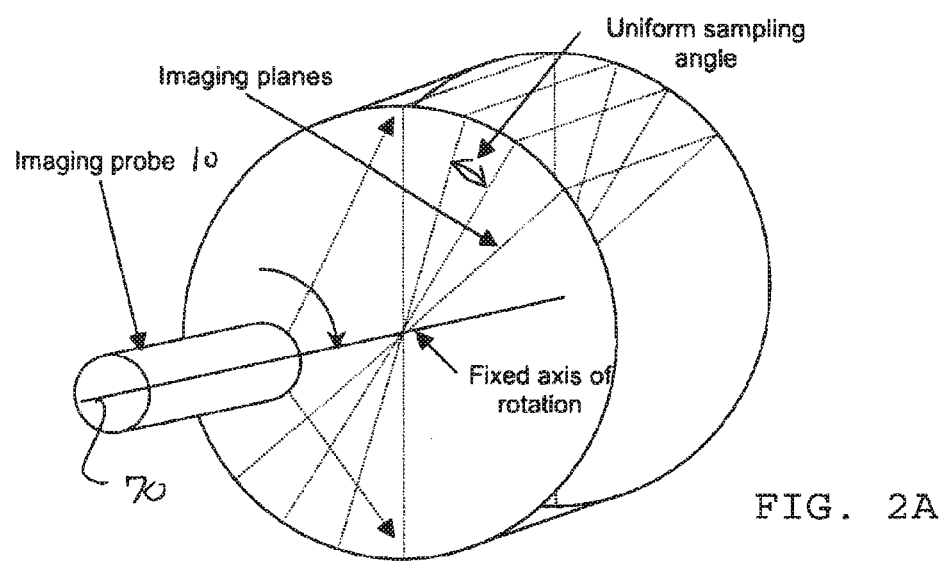
FIGS. 2A and 2B illustrate acquisition of medical images having a single degree of freedom.
Figure 2B:
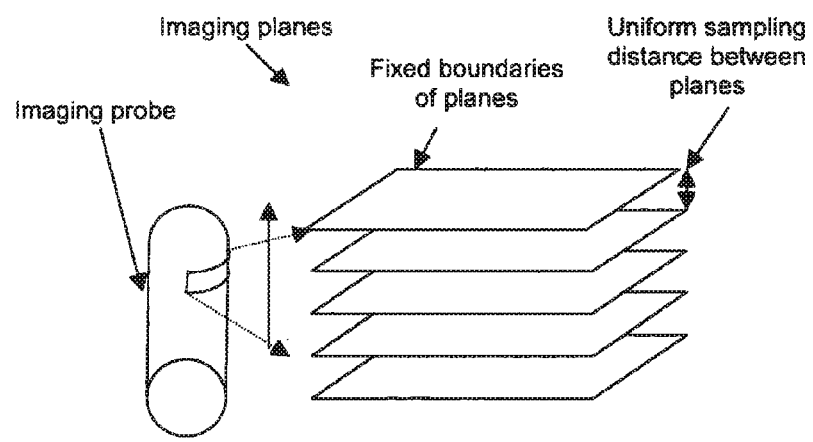

In an automated arrangement, the probe may be affixed to a positioning device (not shown) and a motor may sweep the transducer of the ultrasound probe 10 over a radial area of interest (e.g., around a fixed axis 70 of FIG. 2A). Accordingly, the probe 10 may acquire plurality of individual images while being rotated through the area of interest. Each of these individual image slices may be represented as a two-dimensional image. Alternately, the probe 10 may be linearly advanced to obtain a plurality of uniformly spaced images as is illustrated in FIG. 2B. In both instances, the resulting 2-D image sets may be registered to generate a three-dimensional image. In order to generate a highly accurate 3-D reconstruction, previous interpolation techniques have typically depended heavily on the tolerances on deviation from the assumptions (i.e., that all images are fixed except for a single degree of freedom). However, it is often desirable to utilize a handheld probe to acquire images, for example, just prior to performing a procedure.

Figure 3A:
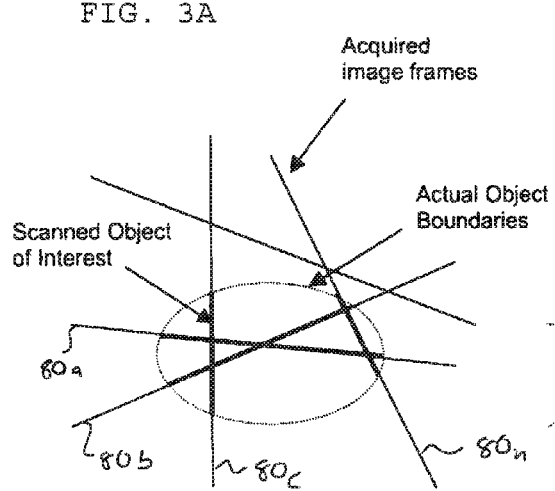
FIGS. 3A-3D illustrate arbitrarily aligned 2-D images and the use of those images to identify the boundaries of an internal object of interest.

Such handheld acquisition, however, often introduces multiple degrees of freedom into the acquired 2-D images. For example, FIG. 3A illustrates a plurality of 2-D images 80*a-n* acquired for an object of interest (e.g., prostate) where the images are not aligned to at least one axis. Further, while performing a procedure or delivering drug to specific part of an organ (or focused surgery such as focusing in narrow regions such as in high frequency ultrasound methods), a user may not need 3-D information in same resolution inside and outside the object. Specifically, the procedure requirements may not need the user to go through a tedious and constrained acquisition of 2-D images, which may take longer for unnecessarily high resolution everywhere in a reconstructed 3-D image, or yield a uniformly low-resolution image. Instead, higher resolution at the region of interest and lower resolution at other places may in some instances be sufficient.

Aspects of the presented systems and methods provide such an option while also allowing for conventional and constrained interpolation and reconstruction strategies. In this method, 2-D images are obtained in an unconstrained fashion (e.g., using handheld imaging devices) while the imaging device is manipulated to scan the object. The user may scan the object in a freehand fashion in various different orientations. See, e.g., FIG. 3A. The orientation and location of the imaging planes are measured using a mechanical or magnetic tracker 14, which may be off-the-shelf or designed specifically for that application. See FIG. 1. The position of the tracker 14 is recorded in relation to a known reference by a reading device 16, which outputs the identified location of the tracker 14 to an imaging system 30 that also receives images from the imaging device 10. The configuration of the reading device may depend upon the type of tracker 14 utilized. For instance, when utilizing a magnetic tracker, the reader may be a magnetic field sensor, which is interfaced to a computer or recording device via an interface box. Mechanical trackers may have a combination of rotary and linear encoders to track the transducer attached to the tracker. Optical trackers have attachment containing LEDs and their position is space is computed using images captured from two cameras at different locations.

The imaging system 30 is operative to correlate the recorded position of the tracker and a corresponding acquired image. As will be discussed herein, this allows for utilizing non-aligned/arbitrary images for 3-D image reconstruction.

That is, the imaging system 30 utilizes the acquired images to populate the 3-D image volume as per their measured locations. In addition to reconstructing the 3-D volume after images are acquired, the method also allows for dynamic refinement at desired regions. That is, a user may acquire additional images at desired locations and the reconstruction method interpolates the additional images into the 3-D volume.

While a significant number of 2-D images typically need to be acquired to generate a 3-D image of reasonably good resolution for an object of interest, it can be time consuming to obtain enough 2-D images to get such resolution. Moreover, it remains a challenge to extract surface from the images in a short time so as to be usable. Without extraction of surface of the object, some of key advantages of 3-D images are lost since the user can no longer visualize the anatomy in a 3-D space without the background being suppressed. As a result, the correspondence of a 2-D live image during the procedure with the previously acquired 3-D image is rendered useless. In order to take full advantage of 1) live image corresponding to a 3-D anatomical object imaged previously, the operator has to 1) acquire a series of 2-D images at a reasonably good resolution and 2) after reconstruction, extract the surface of anatomical object from the 3-D image. Both processes are time-consuming if meaningful results are to be obtained.

A second aspect of the present invention addresses this issue by allowing the user to collect images in a simplified manner (e.g., freehand, just before a procedure). In this aspect, instead of interpolating the pixel intensity values in 3-D image volume from the scanned 2-D image planes, the object itself is interpolated using shape priors. Shape priors refer to a set of information 60 collected previously for a particular anatomical object and includes the mean shape of the object along with statistical information. The statistical information provides the modes of variations in the shape of the object and represents anatomically meaningful interpretations of the shape variability within the population.

Interpolation of 2-D Images in Arbitrary Orientation.

Figure 4A:
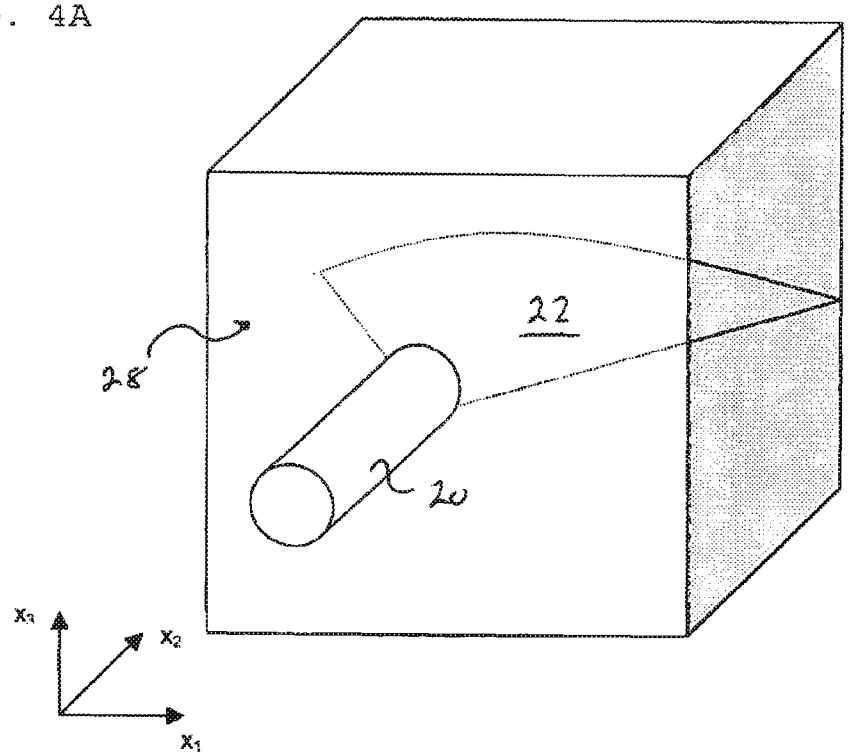
FIGS. 4A and 4B illustrate a coordinate system for a 2-D imaging plane.
Figure 4B:
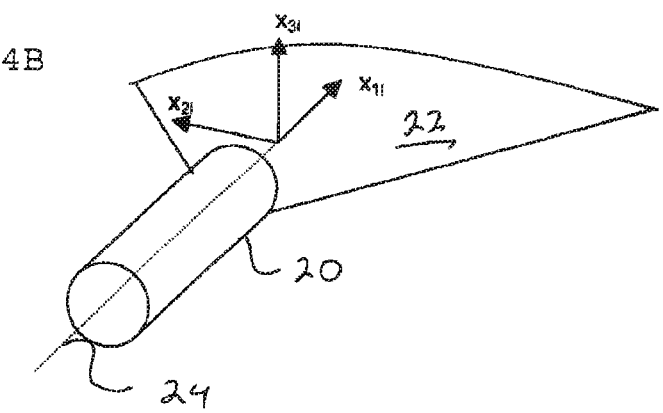

While imaging in freehand or using any constrained or unconstrained method, the tracker provides full information about the 2-D plane being imaged. A normal to the imaging plane and a reference line passing through a known point in the imaging plane are sufficient to describe the imaged plane fully based on the geometry of the imaging device. For example, as illustrated in FIGS. 4A and 4B, which illustrate an end-fire TRUS ultrasound transducer 10, the position of the center of the transducer tip (i.e., provided by a tracker) along with the normal to the image plane 22 and the central axis 24 of the transducer 20 is sufficient to place the 2-D image in a 3-D volume, assuming that the other characteristics such as the depth setting and geometry (rectangular, fan, etc) of 2-D imaging plane are known. In such a case, the tracker output can be measured to provide the location and orientation of the imaging equipment, which in turn provides the normal to imaging plane, central axis 24 of the transducer 20 and the tip of the transducer 20. Based on geometry of the 2-D image observed, its corresponding location in 3-D can be determined using the method presented.

As illustrated, FIG. 4B shows a 2-D imaging slice 22 and its associated co-ordinate system. Letting $X_i'=[x_{1i}'\ x_{2i}'\ x_{3i}']$ represent the co-ordinate system of i-th 2-D image acquired as shown in the figure, where $x_3'$ faces out of plane of the 2-D image slice 22. Then, in frame of reference of the coordinates of image, $x_{3i}'$ is always zero and the center of transducer tip is at the origin.

FIG. 4A illustrates the co-ordinate system for the 3-D image, where origin is selected by the user at the time of initialization of an imaging scan by pointing roughly to the center of the object 28 to be imaged. As shown in the figure, let $X=[x_1\ x_2\ x_3]^t$ represent the coordinates in frame of reference a resulting 3-D image.

Figure 5:
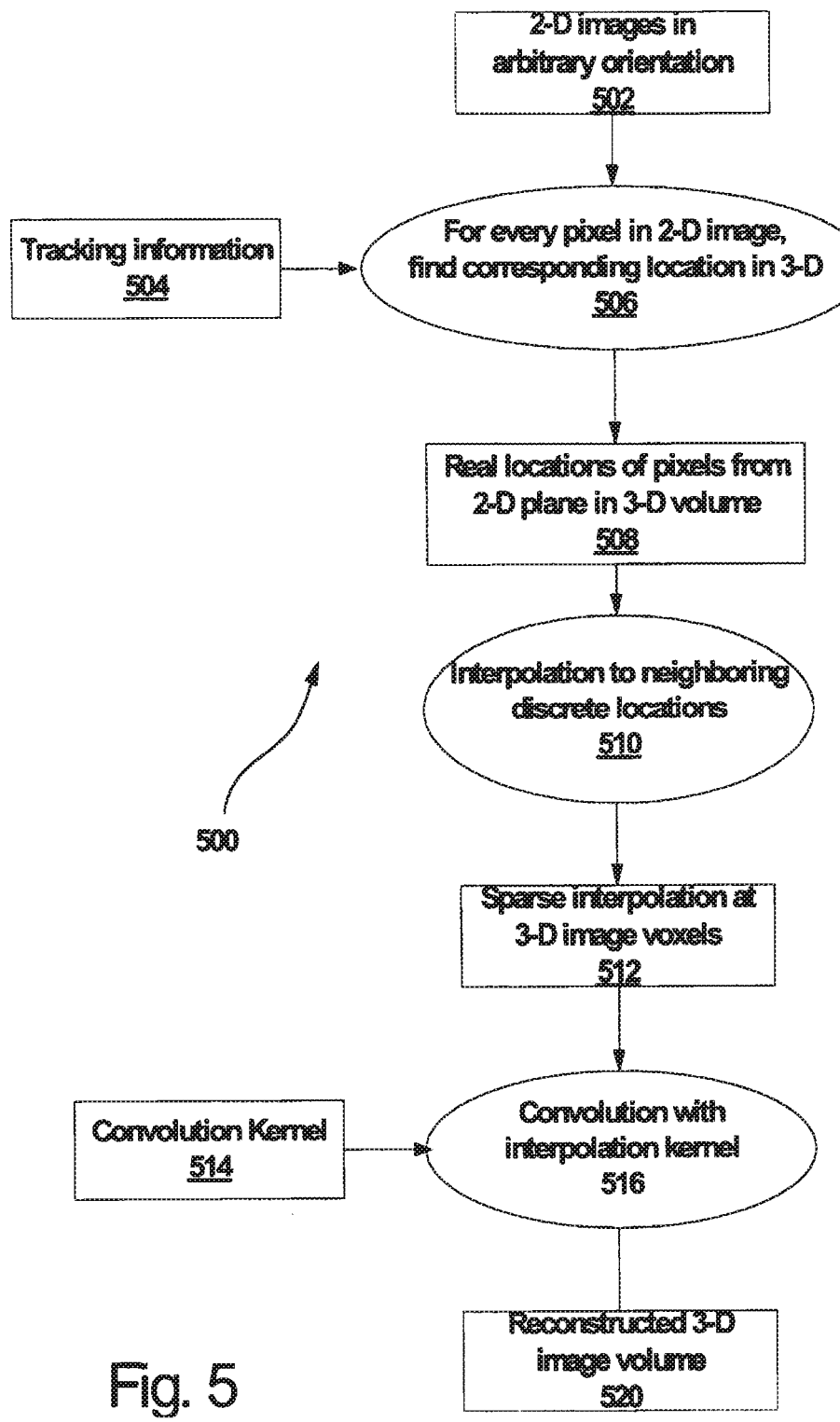
FIG. 5 illustrates a process for reconstructing a 3-D image from arbitrarily oriented 2-D images.

In order to interpolate the images to fill a 3-D space and thereby construct a 3-D image, the 2-D image coordinate system has to be placed in a 3-D image coordinate system. Such a process 500 is illustrated in FIG. 5. Initially, 2-D images, which may have arbitrary orientations, are obtained (502). Tracking information for each image is likewise obtained (504). Then, each pixel in each 2-D image is placed (506) in a corresponding location in a 3-D volume. This is done first by placing the origin of each 2-D image in a frame of reference of a common 3-D volume and then applying the coordinate transformation. The coordination information is obtained by tracking the location and orientation of the imaging transducer using an unconstrained tracker such as a magnetic tracker, freehand mechanical tracker, optical tracker, etc. The co-ordinate transformation simply involves a rotation matrix obtained by solving the following set of linear equations:

$$Rn_i'=n,$$

$$Rt_i'=t,$$

$$Rb_i'=b. \qquad \text{Eq. 1}$$

where, $n_i'=[0\ 0\ 1]^t$ is the unit vector in direction of $x_{3i}'$, $t_i'=[0\ 1\ 0]^t$ represents the unit vector in the direction of $x_{2i}'$ and $b_i'=[1\ 0\ 0]$ is the unit vector in direction of $x_{1i}'$ in frame of reference of the 2-D image. n and t represent the measured normal and tangent unit vectors for the i-th slice and b represents the unit bi-normal representing the cross-product n×t. This information is provided by the tracker.

The rotation matrix R computed above is used to compute the transformation of the coordinate system from the coordinates of the 2-D image into coordinates of the 3-D image. Letting O be the origin of the frame of reference of the 3-D image and O' be the origin of frame of reference of the 2-D image. Then, the overall transformation of coordinate point $(x_i', y_i', z_i')$ from the coordinate system of the 2-D image into the frame of reference of the 3-D image is given by:

$$\begin{pmatrix} x_i \\ y_i \\ z_i \\ 1 \end{pmatrix} = \begin{bmatrix} & & & \Delta x_i \\ & R & & \Delta y_i \\ & & & \Delta z_i \\ 0 & 0 & 0 & 1 \end{bmatrix} \begin{pmatrix} x_i' \\ y_i' \\ z_i' \\ 1 \end{pmatrix} \qquad \text{Eq. 2}$$

where, $(\Delta x_i\ \ \Delta y_i\ \ \Delta z_i) = O - O'.$

At this time, the real location of the 2-D pixels is located (508) in a common 3-D volume. The transformed coordinates do not, in general, lie on a discrete lattice and the intensities at the transformed "real" coordinate locations need to be interpolated (510) onto the neighboring discrete locations. First, the neighboring discrete locations are computed and variables defined as follows:

$x_{li}^d = \mod(x_i) = $ largest integer smaller than $x_i$.

$x_{hi}^d = x_{li}^d + 1 = $ smallest integer greater than $x_i$, if $x_{li}^d \neq x_i$;

-continued $$= x_{li}^d, \text{ if } x_{li}^d = x_i, \text{ and}$$

$$dx_{li} = x_i - x_{li}^d,$$

$$dx_{hi} = x_{hi}^d - x_i.$$

Letting $y_{li}^d$, $y_{hi}^d$, $dy_{li}$, $dy_{hi}$, $z_{li}^d$, $z_{hi}^d$, $dz_{li}$ and $dz_{hi}$ be defined similarly for $x_i$, $y_i$ and $z_i$, respectively. Then, initializing all the intensities in the reconstructed image to be equal to zero and define the following weights to intensities of pixels for 2-D frame i as shown below:

$$w_i(x_{li}, y_{li}, z_{li}) = (1-dx_{li})(1-dy_{li})(1-dz_{li})$$

$$w_i(x_{li}, y_{li}, z_{hi}) = (1-dx_{li})(1-dy_{li})(1-dz_{hi})$$

$$w_i(x_{li}, y_{hi}, z_{li}) = (1-dx_{li})(1-dy_{hi})(1-dz_{li})$$

$$w_i(x_{li}, y_{hi}, z_{hi}) = (1-dx_{li})(1-dy_{hi})(1-dz_{hi})$$

$$w_i(x_{hi}, y_{li}, z_{li}) = (1-dx_{hi})(1-dy_{li})(1-dz_{li})$$

$$w_i(x_{hi}, y_{li}, z_{hi}) = (1-dx_{hi})(1-dy_{li})(1-dz_{hi})$$

$$w_i(x_{hi}, y_{hi}, z_{li}) = (1-dx_{hi})(1-dy_{hi})(1-dz_{li})$$

$$w_i(x_{hi}, y_{hi}, z_{hi}) = (1-dx_{hi})(1-dy_{hi})(1-dz_{hi})$$

Letting $I_i(x, y, z)$ be the intensity of the transformed image at coordinate (x, y, z) based on i-th 2-D image frame. Then, the intensity at a pixel (voxel) location (x,y,z) can be dynamically computed as:

$$I(x, y, z) = \frac{\sum_i w_i I_i(x, y, z)}{\sum_i w_i} \quad \text{Eq. 3}$$

where, the summation is over all the frames (i's in above equation) that contribute to the pixel (x,y,z). This results in a space interpolation (512) of 3-D image voxels. As more and more 2-D frames contribute to the same pixel location in discrete lattice of the 3-D image volume, the intensity gets refined to produce better results.

Once the images are acquired, a Gaussian interpolation filter or other appropriate filter (514) with appropriate window size ($3^3$ to $7^3$, based on image resolution) can be used to interpolate (516) the results to pixels that have not been initialized using Eq. 1 above. The result is that a 3_D image volume may be constructed (518) from the acquired images. If the user wishes to scan portions of image in better resolution, they may acquire more images from the area of interest and the method will dynamically update the intensity values in that location as per Eq. (3).

The method thus, interpolates a 3-D image from 2-D images that are acquired in arbitrary orientations and thereby permits freehand scanning. This may improve the workflow, as it removes need for any locking or constrained tracker. In addition, the dynamic interpolation allows the user to dynamically improve the resolution by acquiring more images from a particular are of interest. The flexibility in choosing different resolution for different regions is another key advantage of the method.

Using Shape Information to Interpolate the Object Surface.

Shape priors are utilized to perform interpolation of a surface for the 3-D image volume. In this method, first, shape statistics are generated and analyzed from a number of actual data sets from the anatomical object in question (e.g., prostate). To do this, a number of images of the anatomical object are collected. The boundaries of the object of interest are then extracted either manually by expert segmentation, or using a semi-automatic or automatic method. The surfaces are then normalized so as to remove the translation, rotation and scaling artifacts. The normalized images are then averaged together by computing mean position of each vertex in the template chosen for computing the mean shape. The shape obtained is run through the same process until convergence. This provides the mean shape of the object and this shape is then registered with all the other shapes in the sample dataset. The registration provides deformation details at each vertex of the image and the statistics of the same are then used to drive the fitting of the mean shape into the shape of the subject.

Figure 3B:
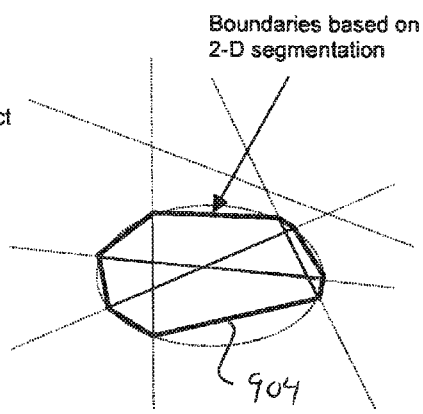
Figure 6:
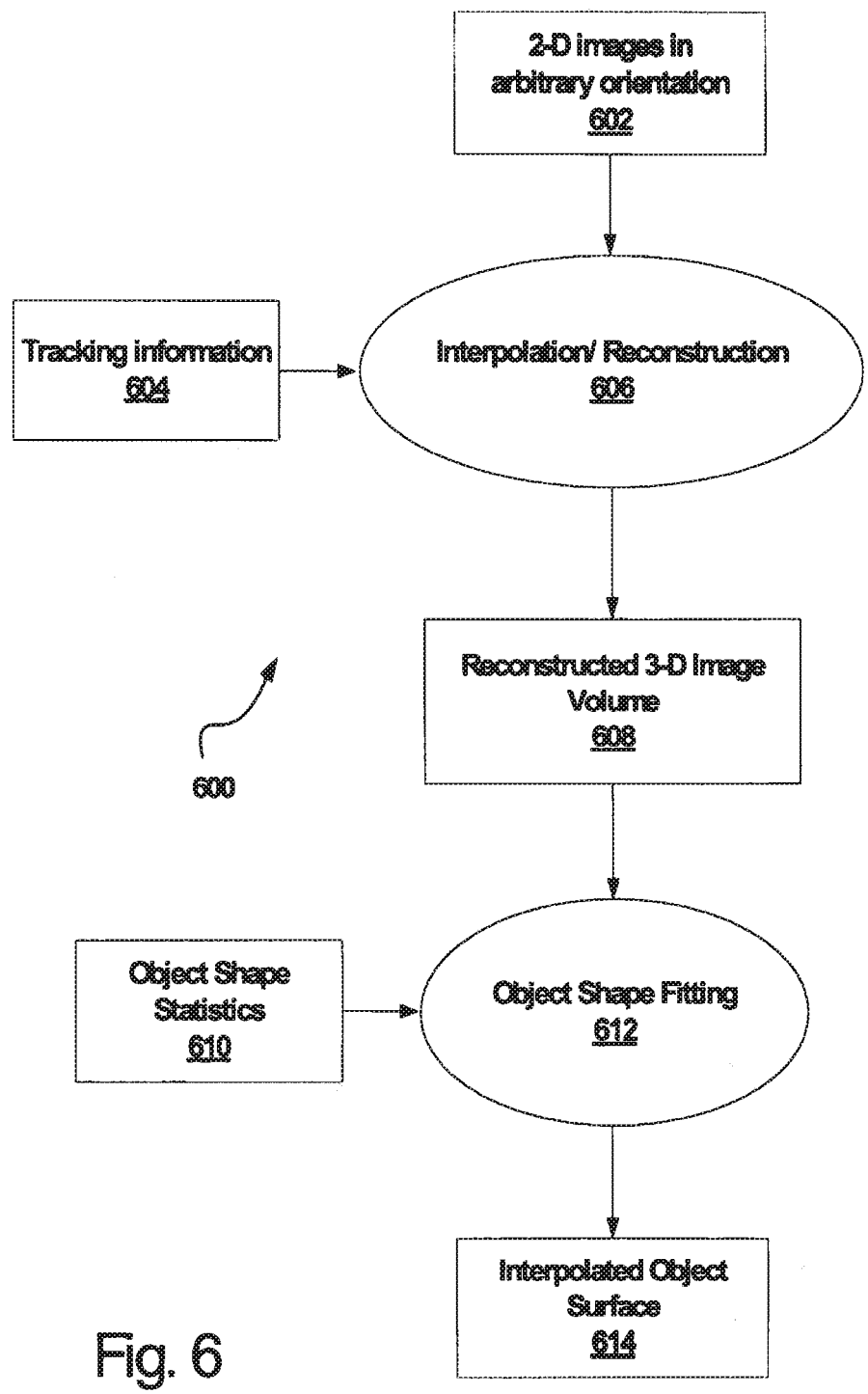
FIG. 6 illustrates a process for use of arbitrarily orienting 2-D images in conjunction with a shape model.

Previously computed statistics may be used to deform the mean shape to fit the 3-D image volume, which may be sparse due to being generated using very few 2-D image planes and/or due to the 2-D images being obtained in different orientations. Conventional segmentation techniques for extraction of surface rely heavily on the resolution of images. Although 2-D segmentation may be possible on individual frames, the combination of these frames together to generate a surface in 3-D using a heuristic approach typically produces artifacts in surface interpolation. Further, due to the limited number of 2-D images boundaries of the 3-D volume based solely on the 2-D images may not provide a useful estimation of the actual boundary of the object. See FIG. 3B. With the presented method however, limited information is supported by the prior knowledge about the shape and the shape prior information is used to fit an entire surface in 3-D such that it still represents the boundaries in the sampled 2-D image but is defined entirely. FIG. 6 shows the overall scheme for combination of the two methods. The images are acquired.

As shown, the process (600) includes acquiring 2-D images (602) and tracking information (604). These elements are utilized to interpolate/reconstruct (606) a 3-D image volume (608), as set forth above. Object shape statistics (610) associated with the object of the 3-D image volume (608) are utilized to fit (612) the mean shape to the 3-D image volume. This generates an object surface (614) that may be output to, for example, a monitor 40 (See FIG. 1) and/or utilized for an image guided procedure or therapy.

The first step is to generate population statistics including a mean shape from a collection of samples from population of the object of interest. This may be done once and may be performed off-line (i.e., at a time before an imaging procedure). The population may correspond to a specific organ, for example: prostate, in which case, a number of images acquired from prostates of different individuals may be used as samples. Larger sample size can capture more variability in the population and hence, a reasonably large sample size should be used to capture the shape statistics. The population may consist of images from different modality.

Figure 7:
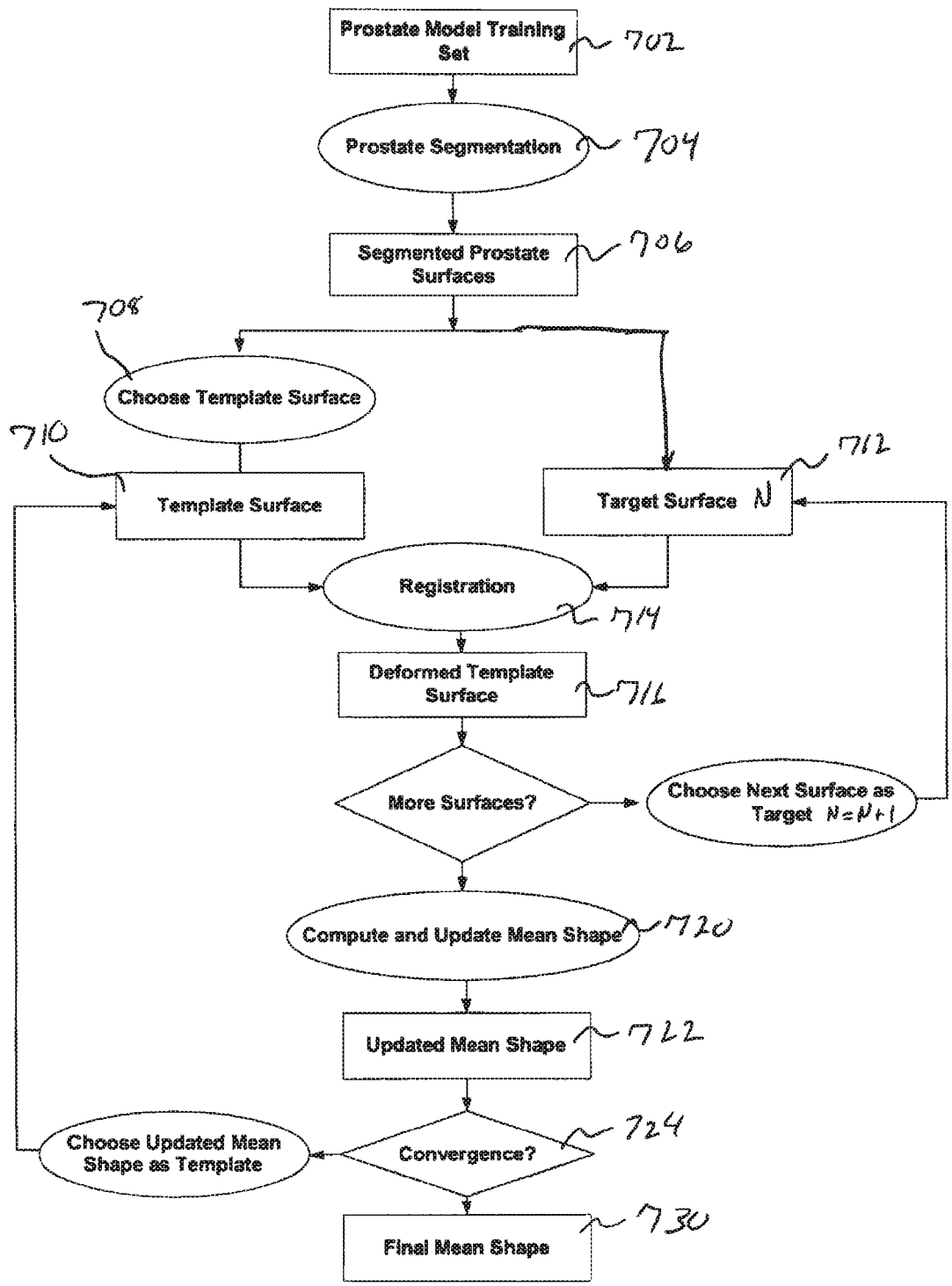
FIG. 7 illustrates generation of a shape model for identifying boundaries of a 3-D object.

FIG. 7 shows the computation of mean shape and capturing the shape statistics from the training dataset (702). First, the surface of the object is extracted/segmented (704) for all the images in the sample dataset. This may be done manually, semi-automatically or automatically. After extraction of surface (706) from all the images through segmentation, one image that best represents the population is chosen (708) as template image (710). The surface of the template is aligned/registered 714 to the current target image 712 using rotation, translation and anisotropic scaling and a mean surface is computed 716. The mean surface is then deformed into every other image in the training set and the mean surface is updated by computing an average again 720 to separate an updated mean shape 722. This process is repeated until convergence to generate a final mean shape 730. A more complete description of computing a mean shape is set forth in co-pending U.S. patent application Ser. No. 11/740,807, entitled, "Improved System and Method for 3-D Biopsy," the contents of which are incorporated herein by reference.

To generate population statistics, the mean surface is warped into all the surfaces in the training set such that the vertex locations of undeformed mean shape and deformed mean surface are known. Letting $V_i$ represent the set of vertices for image i, and $V_\mu$ represent the set of vertices for the mean shape, then the population co-variance matrix is computed as $S=(V_i-V_\mu)^t(V_i-V_\mu)$. The eigen-vectors of the covariance matrix then represent the modes of variations of the shape within the training data. The eigenvalues can then be arranged in descending order such that the eigen vectors representing first few modes of variations represent most of the variability in the population. Specifically, let $S\lambda=p\lambda$, where e represents the vector of all the eigen values and p represents the corresponding eigenvectors. Then, first few eigenvectors be chosen to represent most of variability in the population. In addition, this knowledge can be used to generate more objects from the population, e.g. $V'=V_\mu+pc$, where c is set of weights that determine the differences from mean shape according to modes of allowable variation.

While the theory of shape models is well established, the presented method utilizes the theory to fit a mean surface into the sparse image set acquired such that entire object can be represented using just a few number of 2-D images. Generally, to perform segmentation directly on the image will require a reasonably good resolution of image, which means that a large number of images will need to be acquired and 3-D image space will need to be filled before segmentation can be done. In addition, segmentation in 3-D is computationally demanding and may not be able to be performed within a desirable time. As a result, some techniques resort to segmentation in 2-D and then combining the 2-D segmentations into a surface in 3-D. Such techniques, while faster, obviously suffer from disadvantages of not using the available information fully by neglecting the 3-D interconnectivity.

Figure 3C:
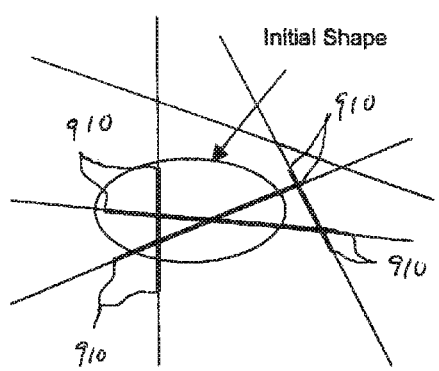
Figure 3D:
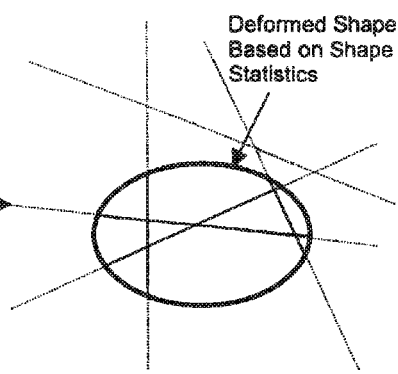

In presented method, a few numbers of images are sufficient to perform a good segmentation of the object. This is achieved by first acquiring a few images that captures the object in various orientations and then placing the mean shape 900 into the reconstructed 3-D image 904. See FIG. 3C. The reconstructed 3-D image will be very sparse with mostly zero values. However, only available 2-D information in various orientations can be used to deform the mean shape 900 into the shape of the scanned object by letting the mean surface deform while following the population deformation characteristics (modes of variations). The deformation optimizes the value of coefficients "c" such that $V'=V_\mu+pc$ yields maximization of intensity gradient at the boundaries of the surface. For instance, the edges 910 of the object as represented by the acquired image frames may be utilized as constraints for defining the mean shape. These edges may be identified using any appropriate segmentation process. In any case, use of the edges 910 allows for closely fitting the mean shape to the actual object boundaries. See FIG. 3D.

Motion Correction in 3-D

In a number of procedures, an image of one modality is scanned in 3-D before the procedure (pre-op) and then a 2-D live image is used to navigate during the procedure. Examples include pre-op MR scan before a surgery (say, brain) and live 2-D ultrasound image while performing the actual surgery. Due to differences in time between the two images, difference in coordinate system, differences in image qualities and deformation of tissue between the images or during the procedure, it is important to align the 2-D live ultrasound image with the previously acquired 3-D images, which may be stored by an imaging device. See FIG. 1. Any motion of patient, instrument or tissue can complicate the problem. Most current techniques align 2-D live image with a stored 3-D image by extracting corresponding 2-D slice from the 3-D image, which is equivalent to a rigid registration between the images. Since the registration is based on only a 2-D image slice, there can be many false minima and robustness is an issue. Moreover, a non-rigid registration that may follow, assumes only in-plane deformation, which captures only a part of actual deformation. In the presented invention, the robustness is improved by using a series of 2-D slices for motion correction such that the registration is based on partial 3-D information rather than purely 2-D information.

The real-time interpolation from arbitrary image planes, as discussed above, easily allows for such a system, where the 2-D live image being acquired is kept in buffer for next few frames. For instance, at any time the 2-D live image slice number is n, and there may always be previous m images kept in a buffer. m may be a small number such as 5-10. In this case, there are more than one slices to be placed in 3-D. Since the data input refresh rate is typically around 30 frames per second, 5-10 slices only means that the data corresponding to a small fraction ($\cong 0.2$ seconds) is being kept in buffer. This immediate previous data, together with current frame provides 5-10 slices in 3-D, that can be correlated with a previously acquired 3-D image. Since there are more slices in different orientation, the robustness is much improved and the live images can be placed in coordinate frame of reference of the 3-D image with more confidence. In addition, if non-rigid registration is needed, the sequence of images provide a much better starting point than just one image and capture deformation in more directions than just along the frame of image acquisition.

Acquisition of Different Modalities and Their Fusion

The image acquisition method discussed above can be used for diagnostic imaging or for biopsy, surgical or image based drug delivery system. The interpolation method may be used to acquire images from different modalities such as ultrasound and elastography. The 2-D image acquired from these modalities can be combined together with the tracking information to place the results in 3-D such that the elastography images can be shown overlaid on the ultrasound data, thus providing additional information to the user. In addition, if a pre-operative MRI scan is available in 3-D, the reconstructed elastographic data can be overlaid onto the structural scan acquired earlier. Likewise, if functional information such as MR spectroscopy is available, the live ultrasound image can be placed in correspondence with the spectroscopy data based on the tracker information and the registration step as discussed above. The registration may be two-step process: rigid, followed by non-rigid. The non-rigid registration may be based on the segmented surface, where a shape model can be used to segment the images in different modalities and the segmented surfaces registered together.

In addition to registering images from different modalities to perform a fusion, the presented method may also be used to study local tissue deformations over time. Many diseases manifest themselves in abnormal tissue deformation and the local deformation can be used for interpreting tissue conditions. As an example, in a repeat prostate biopsy case, a patient image obtained from previous visit may be registered with the image obtained from the repeat visit and the local deformation may be used to observe the abnormal local volume changes in tissue. The local deformation may be a useful indicator of locations of cancer growth. The registration may be mutual information based, intensity based, surface based, landmark based or a combination of any of these. The registration provides the correspondence between the previous image and the current image. The Jacobian value for the deformation map may then be computed and overlaid on the 3-D prostate volume to look at the abnormal localized deformations and any such locations found must be sampled.

The above-noted utilities provide a number of advantages. One primary advantage is that the utilities can construct 3-D images using 2-D images that are acquired in an unconstrained manner (e.g., freehand) where uniform angular or linear spacing between images is no longer required. Likewise, this may result in better workflow as a user no longer needs to obtain images in a constrained environment.

Another advantage is that the utilities allow for flexibility of resolution. In this regard, the user can scan different regions with different resolution thereby providing more flexibility and usage. This also permits fine tuning of an image in real-time. If the user desires better resolution for an acquired image, they may scan more images of the same anatomy and have those images applied to the reconstructed image.

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain best modes known of practicing the invention and to enable others skilled in the art to utilize the invention in such, or other embodiments and with various modifications required by the particular application(s) or use(s) of the present invention. It is intended that the appended claims be construed to include alternative embodiments to the extent permitted by the prior art.

The invention claimed is:

1. A method for use in medical ultrasound imaging, comprising:
   obtaining a first two dimensional ultrasound image of an internal object of interest using a handheld ultrasound device, said first two dimensional ultrasound image having a first image plane and a first three dimensional point of reference obtained from an unconstrained tracker adapted to provide location information in three dimensional space, wherein said first three dimensional point of reference is correlated with said first image plane, and wherein said unconstrained tracker is attached to the handheld ultrasound device;
   obtaining a second two dimensional ultrasound image of the internal object of interest using the handheld ultrasound device, said second two dimensional ultrasound image having a second image plane and second three dimensional point of reference obtained from the unconstrained tracker attached to the handheld ultrasound device, wherein said second three dimensional point of reference is correlated with said second image plane, and wherein said first and second three dimensional points of reference are different and said image planes are non-aligned such that said first and second ultrasound images have arbitrary orientations relative to one another;
   translating pixel information from said first and second two dimensional ultrasound images into a common three dimensional volume; and
   interpolating between information associated with translated pixel information of said two dimensional ultrasound images as disposed within said common three dimensional volume to generate a three dimensional image of the object of interest having different resolution in at least first and second regions of said three dimensional image.

2. The method of claim 1, wherein translating pixel information further comprises:
   applying a coordinate transform to said two-dimensional ultrasound images.

3. The method of claim 2, wherein applying a coordinate transform further comprises:
   for each two-dimensional ultrasound image determining a normal to said image plane;
   defining unit vectors in three directions for said two dimensional image; and
   applying a rotation matrix to said vectors.

4. The method of claim 1, wherein translating said pixel intensity further comprises:
   interpolating pixel intensities from said two-dimensional ultrasound images to discrete locations in said three-dimensional volume.

5. The method of claim 1, further comprising:
   after generating said three dimensional image, obtaining an additional $i^{th}$ two dimensional image having an $i^{th}$ image plane and an $i^{th}$ three dimensional point of reference; and
   incorporating pixel information of said $i^{th}$ image into said three-dimensional image.

6. The method of claim 5, wherein obtaining an additional $i^{th}$ two dimensional image further comprises:
   selectively obtaining a two-dimensional image for a location of interest of said internal object of interest.

7. The method of claim 1, wherein for each image obtaining comprises:
   receiving an image plane from a hand-guided ultrasound imaging device.

8. The method of claim 1, wherein generating a three dimensional image of said object of interest comprises interpolating a surface of said object of interest using statistics associated with said object of interest.

9. The method of claim 8, wherein interpolating said surface comprises:
   fitting a predefined shape model to said pixel information translated into said common three dimensional volume.

10. A method for use in medical ultrasound imaging, comprising:
    obtaining a plurality of arbitrarily aligned two dimensional ultrasound images using a handheld ultrasound device, wherein said images are of an internal object of interest and at least a portion of the images have non-aligned image planes;
    translating pixel intensity information from each of said two dimensional ultrasound images into a common three dimensional volume;
    applying a deformable shape model based on an average corresponding object of a training set population to said pixel intensity information of said common three dimensional volume;
    deforming a surface of said shape model to match boundaries of said internal object of interest within said two dimensional images, wherein said deformed surface of said shape model defines a three dimensional surface for said object of interest in said three dimensional volume; and generating, in response to said deforming, a three-dimensional image of the object of interest having different resolution in at least first and second regions of said three dimensional image.

11. The method of claim 10, wherein shape statistics of said training set population are utilized to fit said predefined shape model to said pixel intensity information.

12. The method of claim 10, wherein boundaries identified within said two dimensional images form constraints for deforming said surface of said predefined shape model.

13. The method of claim 10, further comprising:
performing a three dimensional segmentation of said object of interest using said three dimensional surface as an initial surface boundary.

* * * * *